(12) United States Patent
Sielcken et al.

(10) Patent No.: US 7,087,797 B2
(45) Date of Patent: Aug. 8, 2006

(54) CONTINUOUS HYDROFORMYLATION PROCESS

(75) Inventors: Otto Erik Sielcken, Sittard (NL); Hubertus Adrianus Smits, Maastrich (NL); Imre Toth, Geleen (NL)

(73) Assignee: DSM IP Assets B.V., Heerlen (NL)

( * ) Notice: Subject to any disclaimer, the term of this patent is extended or adjusted under 35 U.S.C. 154(b) by 82 days.

(21) Appl. No.: 10/474,679

(22) PCT Filed: Apr. 11, 2002

(86) PCT No.: PCT/NL02/00236

§ 371 (c)(1), (2), (4) Date: Mar. 31, 2004

(87) PCT Pub. No.: WO02/083613

PCT Pub. Date: Oct. 24, 2002

(65) Prior Publication Data

US 2004/0152924 A1 Aug. 5, 2004

(30) Foreign Application Priority Data

Apr. 13, 2001 (EP) .................................. 01201370

(51) Int. Cl.
*C07C 45/50* (2006.01)

(52) U.S. Cl. ..................................... 568/451; 568/454
(58) Field of Classification Search ................ 568/451, 568/454

See application file for complete search history.

(56) References Cited

U.S. PATENT DOCUMENTS

| | | | | |
|---|---|---|---|---|
| 3,527,809 A | 9/1970 | Pruett | .......................... | 260/604 |
| 4,518,809 A | 5/1985 | Forster | ........................ | 568/840 |
| 4,528,403 A | 7/1985 | Tano | ............................ | 568/454 |
| 4,668,651 A | 5/1987 | Billig | ........................... | 502/158 |
| 4,769,498 A | 9/1988 | Billig | ........................... | 568/454 |
| 4,774,361 A | 9/1988 | Maher | ......................... | 568/454 |
| 5,288,918 A | 2/1994 | Maher | ......................... | 568/454 |
| 5,426,238 A | 6/1995 | Mori | ........................... | 568/454 |
| 6,172,267 B1 * | 1/2001 | Urata et al. | ................. | 568/454 |

* cited by examiner

*Primary Examiner*—Sikarl A. Witherspoon
(74) *Attorney, Agent, or Firm*—Mayer, Brown, Rowe & Maw LLP

(57) ABSTRACT

A continuous hydroformylation process for forming an aldehyde comprising 1) reacting an olefinically unsaturated compound containing from 2 to 30 carbon atoms with carbon monoxide and hydrogen in the presence of a rhodium-bisphosphite ligand complex catalyst and 2) distilling a mixture comprising at least a part of the catalyst of 1), wherein the distilling is performed in the substantial absence of molecular hydrogen.

14 Claims, 1 Drawing Sheet

CONTINUOUS HYDROFORMYLATION PROCESS

CROSS REFERENCE TO RELATED APPLICATION

This application is the National Phase of International Application PCT/NL02/00236 filed Apr. 11, 2002 which designated the U.S., and that International Application was published under PCT Article 21(2) in English.

The invention relates to a continuous hydroformylation process for forming an aldehyde comprising 1) reacting an olefinically unsaturated compound containing from 2 to 30 carbon atoms with carbon monoxide and hydrogen in the presence of a rhodium-bisphosphite ligand complex catalyst, and 2) distilling a mixture comprising at least a part of the catalyst of 1).

It is well known in the art that organophosphites may be employed as catalyst ligands for rhodium based hydroformylation catalysts and that such catalysts exhibit exceptional activity and regioselectivity for producing aldehydes via olefin hydroformylation. For instance, U.S. Pat. Nos. 4,668,651 and 4,769,498 fully detail such hydroformylation.

However, despite the benefits attendant with such rhodium-organophosphite complex catalyzed hydroformylation processes, stability of the ligand and catalyst remains a primary concern. Although hydroformylation processes are performed at moderate temperatures (e.g., <110° C.), heating rhodium organophosphite catalysts above these temperatures has led to decomposition of the catalyst and ligand and has generally resulted in irreversible rhodium metal loss. For example U.S. Pat. No. 5,288,918 describes the decomposition of rhodium bisorganophosphite complexes and ligands which occurs as the result of hydrolysis at elevated temperatures. As a result of this decomposition, the activity and efficiency of the hydroformylation process are lowered and the cost of operating a hydroformylation facility is greatly increased.

It has been found that the thermal decomposition of rhodium bisorganophosphite complexes is most apparent during the distillation phase of the hydroformylation process. As a result of the high boiling points of the product aldehydes, high temperatures are generally required to vaporize these compounds so they may be separated and isolated from other materials which are present in the reaction mixture. These harsh conditions inevitably result in rhodium catalyst decomposition during product isolation. Although techniques aimed at aldehyde separation at lower temperatures, such as reduced pressure distillation, have met with limited success, a hydroformylation process which could allow for aldehyde collection under these forcing conditions would constitute a welcome advance in hydroformylation catalysis.

The object of the invention is to reverse or at least minimize catalyst deactivation or decomposition of rhodium-bisphosphite complex catalysts.

This object is achieved by performing the distilling in the substantial absence of molecular hydrogen.

In a preferred embodiment of the present invention the rhodium-bisphosphite complex catalyst comprises a bisphosphite ligand of a formula selected from the group consisting of:

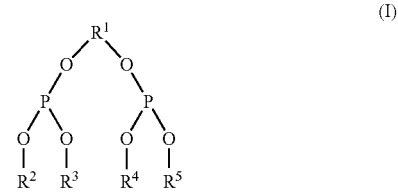

(I)

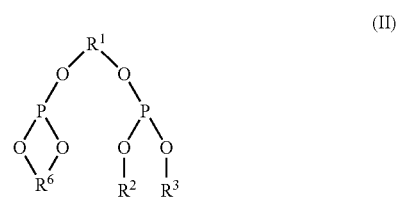

(II)

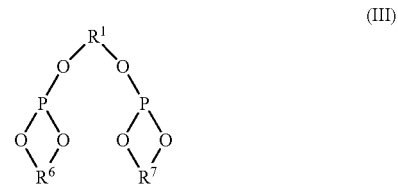

(III)

wherein each $R^1$ represents a divalent radical selected from a group consisting of alkylene, alkylene-$(Q)_n$-alkylene, arylene and arylene-$(Q)_n$-arylene, and wherein each alkylene radical individually contains from 2 to 18 carbon atoms and is the same or different, and wherein each arylene radical individually contains from 6 to 18 carbon atoms and is the same or different; wherein each Q individually represents a divalent bridging group of —O— or —CR'R"- wherein each R' and R" radical individually represents hydrogen or a methyl radical; and wherein each n individually has a value of 0 or 1, wherein $R^2$, $R^3$, $R^4$, and $R^5$ might be the same or different and each is individually represented by the structure of (VI) or (VII),

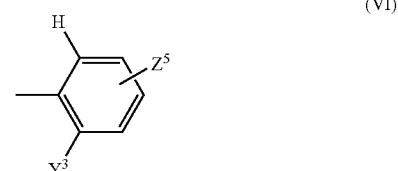

(VI)

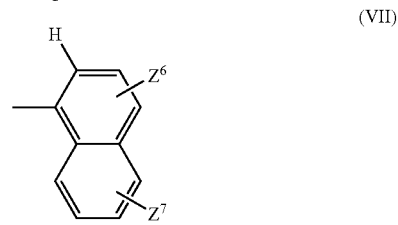

(VII)

wherein R⁶ and R⁷ may be the same or different and each is individually represented by the structure of (VIII) or (IX),

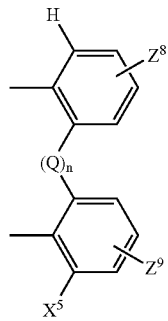
(VIII)

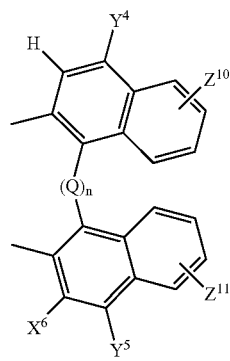
(IX)

wherein X⁵ and X⁶ might be the same or different and each individually represents an organic radical, wherein Y³, Y⁴ and Y⁵ are the same or different and each represents a hydrogen or alkyl radical, wherein Z⁵, Z⁶, Z⁷, Z⁸, Z⁹, Z¹⁰ and Z¹¹ may be the same or different and each represent a hydrogen or an organic radical placed at any remaining position of the aryl rings.

In a more preferred embodiment of the present invention, R¹ is represented by the structure of (IV), (V),

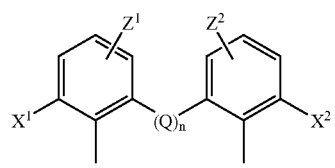
(IV)

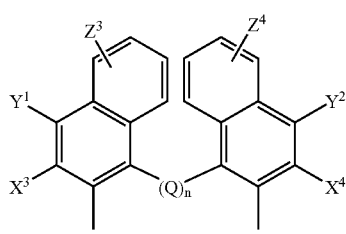
(V)

(VIII), (IX), wherein (Q)ₙ is the same as above, wherein X¹, X², X³, X⁴, X⁵ and X⁶ might be the same or different and each individually represents a hydrogen or an organic radical, wherein Y¹, Y², Y⁴ and Y⁵ are the same or different and each represents a hydrogen or alkyl radical, wherein Z¹, Z², Z³, Z⁴, Z⁸, Z⁹, Z¹⁰ and Z¹¹ might be the same or different and each represent a hydrogen or an organic radical placed at any remaining position of the aryl rings.

In an even more preferred embodiment of the present invention R¹ is represented by the structure of (IV), (V), (VIII), (IX), wherein (Q)ₙ is the same as above, wherein X¹ is the same as X² and Z¹ is the same as Z² in Formula (IV), X³ is the same as X⁴, Z³ is the same as Z⁴, and Y¹ and Y² are hydrogen radicals in Formula (V), Z⁸ is the same as Z⁹ in Formula (VIII), Z¹⁰ is the same as Z¹¹ and Y⁴ and Y⁵ are hydrogen radicals in Formula (IX).

Still more preferably said hydroformylation process is performed wherein said ligand used is chosen from the group consisting of [3,3'-bis(t-butyl)-5,5'-dimethoxy-1,1'-biphenyl-2,2'-diyl]-bis(oxy)]-bis(dibenzo[d,f][1,3,2])dioxaphosphepin, 3,3'-bis(carboxyisopropyl)-1,1'-binaphthyl-2,2-diyl-bis[bis(1-naphthyl)]phosphite and 3,3'-bis(carboxymethyl)-1,1'-binaphthyl-2,2'-diyl-bis[bis(2,5-di-t-butyl)]phosphite.

In a preferred embodiment of the present invention, the total amount of molecular hydrogen present in the distillation mixture as dissolved and complexed hydrogen is no more than 2 ppm, relative to the total weight of the distillation mixture. Preferably it is below 1 ppm, and still more preferably it is below 0.1 ppm.

In another embodiment of the process according to the present invention, the molecular hydrogen content is removed from the mixture to be distilled prior to distillation this mixture. In accordance with preferred embodiments of the invention, hydrogen can be removed by stripping the mixture to be distilled with an inert gas prior to distillation said mixture Alternately, carbon monoxide can be used for stripping prior to distillation of said mixture.

In another embodiment of the process according to the present invention, the molecular hydrogen is removed from the mixture to be distilled by adding an olefin and/or carbon monoxide to the mixture prior to distillation of said mixture.

Still another embodiment of the present invention comprises a hydroformylation process comprising: reacting an olefinically unsaturated compound comprising from 2 to 30 carbon atoms with carbon monoxide and hydrogen in the presence of a rhodium-bisphosphite complex catalyst to produce a mixture to be distilled comprising an aldehyde reaction product or products and a catalyst; reducing or eliminating the amount of hydrogen in the mixture to be distilled; and separating aldehyde product from the catalyst from the mixture to be distilled. Without wishing to be bound to any particular theory it is believed that the rhodium-bisphsophite ligand complex catalyst has at least a first and second state, the said second state is more thermally and/or hydrolytic stable than the first state, and reducing or eliminating the amount of hydrogen in the mixture to be distilled allows for most or all of the catalyst in the mixture to be distilled to be in a more thermally and/or hydrolytic stable state.

Figure 1:
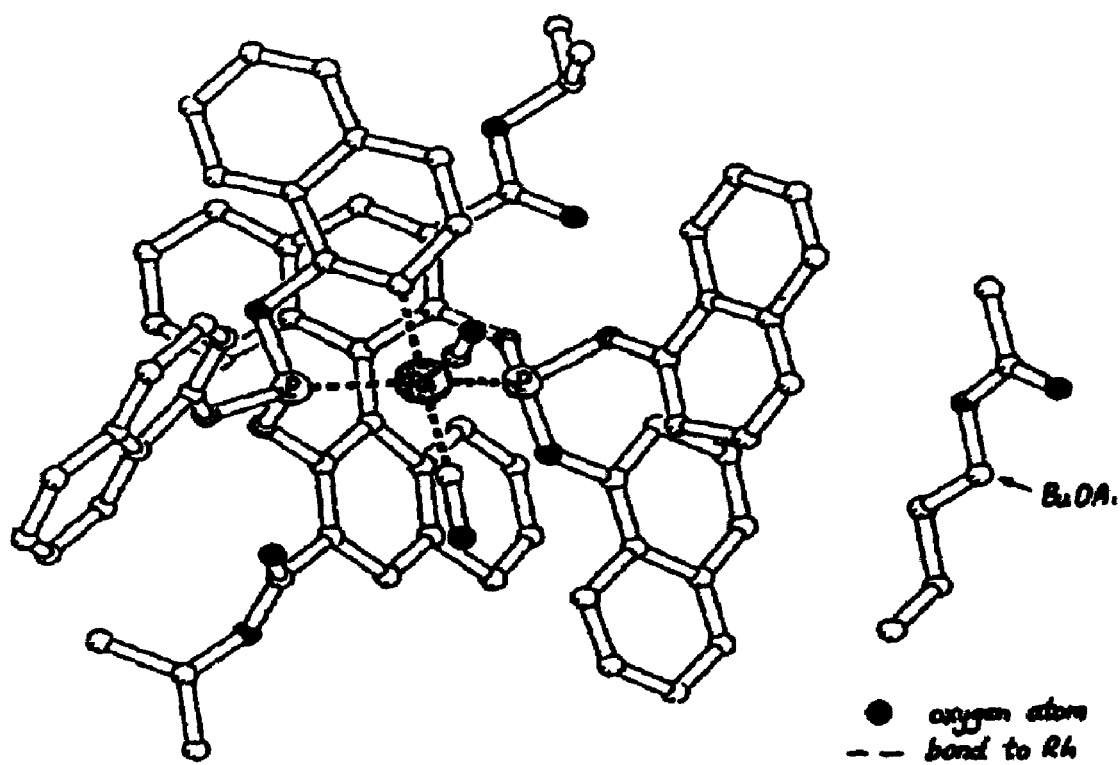
FIG. 1 is a description of an x-ray structure of dicarbonyl orthometallated Rh-naphthol-3 complex.

A rhodium bisphospite complex catalyzed hydroformylation reaction typically involves the exposure of an olefinically unsaturated compound to molecular hydrogen and carbon monoxide in the presence of a rhodium catalyst, to obtain one or more product aldehydes. These products must be separated from remaining olefins, catalyst, excess phosphite, optional solvent, and any other compounds which may be present in the reaction mixture. Perhaps the most common method of separating these product aldehydes from the reaction mixture is by distillation of the reaction mixture. As a result, continuous hydroformylation processes provide for at least a portion of the reaction mixture to be heated, so as to separate the desired product aldehydes from the remaining components of the reaction mixture. Yet the heat which is required to successfully distill the product aldehyde is often damaging to the rhodium catalyst necessary for the reaction. The often irreversible degradation of these catalysts which results from exposure to high temperatures greatly increase the costs of such reaction by requiring increased consumption of precious rhodium metal, and expensive bisphosphite ligands, as well as lower efficiency. Thus the inventors of the present invention sought a means by which a rhodium complex catalyst may be protected from the high temperatures required during distillation.

Accordingly, the subject invention encompasses reversing or minimizing the catalyst deactivation which can occur in rhodium-bisphosphite complex catalyzed hydroformylation processes for producing aldehydes, by carrying out the distillation phase of said process in the absence of molecular hydrogen. The term substantial absence, as used herein, is understood to mean a maximum concentration of 2 parts per million (ppm) of dissolved and complexed hydrogen in the distillation mixture, relative to the total weight of the distillation mixture. More preferably, the hydrogen concentration within the distillation mixture is less than 1 ppm, and still more preferably the hydrogen concentration is less than 0.1 ppm, relative to the total weight of the distillation mixture. The term distillation mixture is defined as all substances contained within the distillation vessel. The term mixture to be distilled is the mixture which is fed to a distillation zone. In particular, the mixture to be distilled is the mixture which is fed to the distillation zone in which aldehyde product is distilled in one or more stages. In this distillation zone aldehyde product and other volatile materials are recovered in vaporous form and the non-volatalized rhodium catalyst containing residue being recycled to the reaction zone.

As stated above, the activity of the rhodium-bisphosphite catalyst has been enhanced by performing the distillation phase of the hydroformylation process after first removing molecular hydrogen from the mixture to be distilled. Without wishing to be bound to any exact theory or mechanistic discourse, it appears that the structural features of certain bisphosphite ligands which make them such beneficially unique hydroformylation catalyst promoters may also provide a pathway which may allow the rhodium-bisphospite catalyst to be thermally protected during the demanding distillation step. Without wishing to be bound to any theory, it is believed that the substituent organic groups employed on the bisorganophosphite ligand are capable of reacting with the metal to form the "orthometallated" product (XI), under the conditions present in the hydroformylation process. This result is summarized by equation (1).

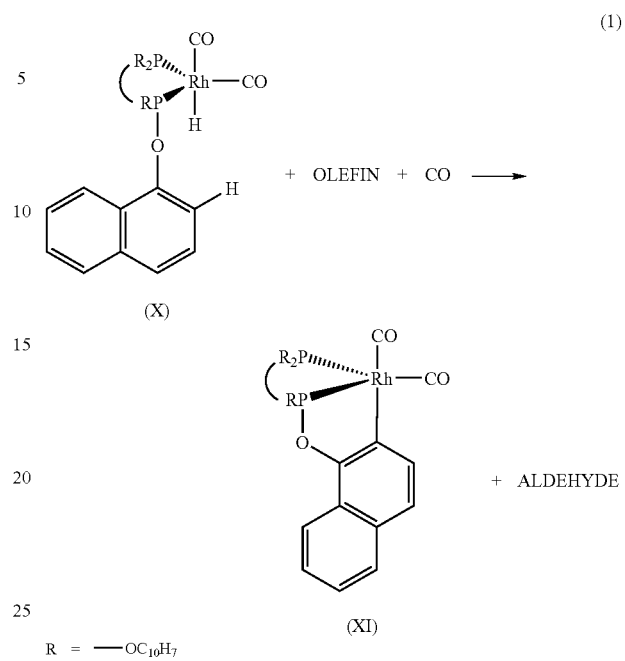

Complex (XI), after isolation, was found to be more stable, that is, less reactive towards ligand decomposition and/or hydrolysis. Furthermore, complex (XI) was found, independently, to undergo a reversible reaction with molecular hydrogen to form Complex (X), as shown in equation (2).

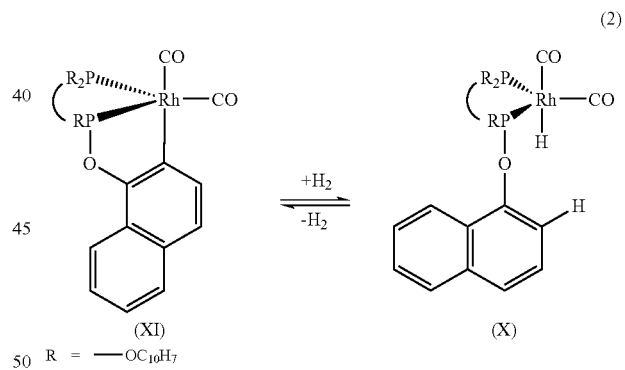

These results suggest that during the hydroformylation reaction the rhodium species will be available for catalysis as the more catalytically active complex (X). However, during the intense heating required during the distillation phase of the hydroformylation process, such a fragile species is thought to undergo decomposition. Therefore, as the results of equation (2) suggest, judicious choice of distillation conditions, such as those which first remove molecular hydrogen prior to distillation may allow the rhodium catalyst to be present as the more thermally stable complex (XI) and thus avoid the observed catalyst decomposition of these systems. However, because the hydroformylation reaction is typically performed with a large excess of molecular hydrogen present, a separate step by which the hydrogen is removed from the mixture to be distilled is required.

Several techniques are available to remove molecular hydrogen from the distillation mixture and/or from the mixture to be distilled. Said hydrogen may be removed from the distillation mixture by employing high vacuum in the distillation column. However, as shown below in Example 8, employing a high vacuum in the range of 0.01–0.001 psia above said distillation mixture is not sufficient to eliminate the dissolved and coordinated hydrogen content in the distillation mixture. Thus, it is preferable to remove the hydrogen content from the mixture to be distilled prior to distillation by using another technique.

Said hydrogen may also be removed from the mixture to be distilled by stripping the mixture with an inert gas such as nitrogen or argon prior to the distillation. More preferably, such stripping is conducted with CO gas before distillation. The stripping with an inert gas or CO gas can be carried out at any practical temperature and pressure. Thus the stripping can be carried out between 0.1–1000 psia pressure and between 40 and 150° C. Preferably, the stripping is carried out at 1–100 psia pressure and 80–120° C. temperature. The required stripping time necessary to remove hydrogen present within the mixture to be distilled will depend on the applied temperature and pressure, as well as on the concentration of hydrogen in the mixture to be treated. The required stripping time can be determined for example by monitoring the concentration of compounds (X) and (XI) by $^{31}P$ NMR spectroscopy.

If CO gas is selected for hydrogen stripping, then the required stripping time will also depend on the olefin concentration in the mixture to be treated. This is due to the fact that, under conditions of excess CO, olefins can react with residual hydrogen present in the reaction medium via the hydroformylation reaction. Accordingly, shorter stripping times are obtained when using CO, rather than with an inert gas.

Likewise, the addition of an olefinic substrate to the mixture to be stripped can shorten the required stripping time. This phenomenon is thought to occur because the addition of an olefin will increase the rate of the hydroformylation reaction, and thus favor the consumption of residual hydrogen present in the mixture to be stripped. The added olefin may be the same or different from the olefin used in the hydroformylation reactors. Preferably, the olefin used as the starting olefin in the desired hydroformylation reaction is the olefin added to enhance hydrogen removal. Preferably, the olefin/Rh ratio is at least 5/1. More preferably, the olefin/Rh ratio is at least 20/1.

The residual hydrogen content of the mixture to be distilled may also be removed by treating the mixture containing the olefinic substrate with CO gas without stripping. For example, the reaction mixture obtained from the hydroformylation reactor(s) can be treated with pressurized CO in a separate reactor before the distillation. Generally, the latter approach is favorable to stripping as it can decrease the amount of CO being used and recycled. There are different technological options for the placement of such reactor for the CO treatment between the hydroformylation reactors and distillation column(s) in a continuous hydroformylation process. For example, the reactor for CO treatment can be coupled to the hydroformylation reactor(s) prior or after a depressurizing vessel. However, anyone skilled in the art can determine the optimal placement of such CO treatment unit in a continuous hydroformylation process. The reactor for the CO treatment can be used at any practical temperature or pressure. Thus, for example, the CO treatment can be carried out by using CO pressures between 10–1000 psia and reaction temperatures between 40 and 150° C. Preferably, the CO treatment is carried out by using CO pressures between 20 and 300 psia and reaction temperatures between 80 and 120° C. The required residence time in such a CO-treatment unit will depend on the applied temperature and pressure, as well as on the concentration of hydrogen and olefin in the mixture to be treated.

As stated above, consumption of residual hydrogen in the presence of excess CO will be accelerated by increasing the concentration of the olefinic substrate. Furthermore, as in the present case the residual hydrogen content is removed mostly by hydroformylation and to a much lesser extent by hydrogenation of the olefinic substrate, it is preferable to use a higher concentration of the olefinic substrate than that of residual hydrogen in the mixture to be treated in order to facilitate hydrogen removal. Thus, when the ratio of the olefin to the residual hydrogen present as free and coordinated hydrogen is lower than 1/1, or the olefin/Rh ratio is lower than 5/1 in the mixture to be treated with CO, it is preferable to add an additional amount of olefin. More preferably, the ratio of olefin to the residual hydrogen is set at least to 5/1 and the ratio of olefin to Rh is set at least 20/1 by adding additional amount of olefin to the mixture to be treated when necessary. The added olefin might be the same or different from the olefin used in the hydroformylation reactors. Preferably, the same olefin is added as the one being hydroformylated in the main process. The required residence time in the reactor for the removal of residual hydrogen content could be determined by anyone skilled in the art, for example by following the bisphosphite-Rh-hydride concentration by $^{31}P$ NMR spectroscopy.

Illustrative rhodium-bisphosphite complex catalyzed continuous hydroformylation processes in which such catalyst deactivation may occur include hydroformylation processes such as described, e.g., in U.S. Pat. Nos. 4,668,651; 4,774,361; 4,769,498; and 5,288,918 wherein the bisphosphite ligand is a ligand selected from the class consisting of Formulas (I) and (II) above, the entire disclosures of said patents being incorporated herein by reference thereto. Thus such hydroformylation processes and the conditions thereof are well known and it is to be understood that the particular manner in which the hydroformylation reaction is carried out and particular hydroformylation reaction conditions employed may be varied widely and tailored to meet individual needs and produce the particular aldehyde product desired.

In general, such hydroformylation reactions involve the production of aldehydes by reacting an olefinic compound with carbon monoxide and hydrogen in the presence of a rhodium-bisphosphite complex catalyst in a liquid medium that also contains a solvent for the catalyst. The process may be carried out in a continuous single pass mode or more preferably in a continuous liquid catalyst recycle manner. The recycle procedure generally involves withdrawing a portion of the liquid reaction mixture containing the catalyst and aldehyde product from the hydroformylation reaction zone, either continuously or intermittently, and distilling aldehyde product therefrom in one or more stages, in a separate distillation zone in order to recover aldehyde product and other volatile materials in vaporous form, the non-volatilized rhodium catalyst containing residue being recycled to the reaction zone. Likewise, the recovered non-volatilized residue containing the rhodium catalyst can be recycled with or without further treatment to the hydroformylation zone in any conventional manner desired. Accordingly, the processing techniques of this invention may correspond to any known processing techniques such as heretofore employed in conventional liquid catalyst recycle hydroformylation reactions.

As noted above, the continuous hydroformylation process of this invention involves the use of a rhodium-bisphosphite ligand complex catalyst as described herein. Of course mixtures of such catalysts can also be employed if desired. The amount of rhodium-phosphite complex catalyst present in the reaction medium of a given hydroformylation process encompassed by this invention need only be that minimum amount necessary to provide the given rhodium concentration desired to be employed and which will furnish the basis for at least the catalytic amount of rhodium necessary to catalyze the particular hydroformylation process involved such as disclosed e.g. in the above-mentioned patents. In general, rhodium concentrations in the range of from about 10 ppm to about 1000 ppm, calculated as free rhodium, in the hydroformylation reaction medium should be sufficient for most processes, while it is generally preferred to employ from about 10 to 500 ppm of rhodium and more preferably from 25 to 350 ppm to rhodium.

In addition to the rhodium-bisphosphite ligand complex catalyst the hydroformylation process encompassed by this invention may be carried out in the presence of free bisphosphite ligand, i.e. ligand that is not complexed with the rhodium metal of the complex catalyst employed. Said free bisphosphite ligand may correspond to any of the above-defined bisphosphite ligands discussed above as employable herein. When employed it is preferred that the free bisphosphite ligand be the same as the bisphosphite ligand of the rhodium-bisphosphite complex catalyst employed. However, such ligands need not be the same in any given process. Moreover, while it may not be absolutely necessary for the hydroformylation process to be carried out in the presence of any such free bisphosphite ligand, the presence of at least some amount of free bisphosphite ligand in the hydroformylation reaction medium is preferred. Thus the hydroformylation process of this invention may be carried out in the absence or presence of any amount of free bisphosphite ligand, e.g. up to 100 moles, or higher per mole of rhodium metal in the hydroformylation reaction medium. Preferably the hydroformylation process of this invention is carried out in the presence of from about 1 to about 50 moles of bisphosphite ligand, and more preferably from about 1 to about 4 moles of bisphosphite ligand, per mole of rhodium metal present in the reaction medium; said amounts of bisphosphite ligand being the sum of both the amount of bisphosphite ligand that is bound (complexed) to the rhodium metal present and the amount of free (non-complexed) bisphosphite ligand present. Of course, if desired, make-up or additional bisphosphite ligand can be supplied to the reaction medium of the hydroformylation process at any time and in any suitable manner, e.g. to maintain a predetermined level of free ligand in the reaction medium.

The hydroformylation reactions encompassed by this invention may also be conducted in the presence of an organic solvent for the rhodium-bisphosphite complex catalyst and any free bisphosphite ligand that might be present. Any suitable solvent which does not unduly adversely interfere with the intended hydroformylation process can be employed. Illustrative suitable solvents for rhodium catalyzed hydroformylation processes include those disclosed e.g. in U.S. Pat. No. 4,668,651. Of course mixtures of one or more different solvents may be employed if desired. Most preferably the solvent will be one in which the olefinic starting material, catalyst, and weakly acidic additive if employed, are all substantially soluble. In general, it is preferred to employ aldehyde compounds corresponding to the aldehyde products desired to be produced and/or higher boiling aldehyde liquid condensation by-products as the primary solvent, such as the higher boiling aldehyde liquid condensation by-products that are produced in situ during the hydroformylation process. Indeed, while one may employ any suitable solvent at the start up of a continuous process, the primary solvent will normally eventually comprise both aldehyde products and higher boiling aldehyde liquid condensation by-products due to the nature of such continuous processes. Such aldehyde condensation by-products can also be preformed if desired and used accordingly. Of course, the amount of solvent employed is not critical to the subject invention and need only be that amount sufficient to provide the reaction medium with the particular rhodium concentration desired for a given process. In general, the amount of solvent may range from 0 percent by weight up to about 95 percent by weight or more based on the total weight of the reaction medium.

The distillation and separation of the desired aldehyde product from the rhodium-bisphosphite complex catalyst containing product solution may take place at any suitable temperature desired. In general it is recommended that such distillation take place at low temperatures, such as below 150° C., and more preferably at a temperature in the range of from about 50° C. to about 130° C., and most preferably up to about 115° C. It is also generally recommended that such aldehyde distillation take place under reduced pressure, e.g. a total gas pressure that is substantially lower than the total gas pressure employed during hydroformylation when low boiling aldehydes (e.g. $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium and then pass said liquid medium which now contains a much lower syn gas concentration than was present in the hydroformylation reaction medium to the distillation zone e.g. vaporizer/separator, wherein the desired aldehyde product is distilled. In general distillation pressures ranging from vacuum pressures up to a total gas pressure of about 50 psia should be sufficient for most purposes.

The improvement in the hydroformylation catalytic activity of a rhodium-bisphosphite complex catalyst obtained according to this invention may be determined and confirmed by any suitable conventional procedure for ascertaining an increase in the productivity of the process. Preferably the process of this invention may be easily evaluated by carrying out comparative hydroformylation reactions and continuously monitoring their rates. The difference in hydroformylation rate (or difference in catalyst activity) may then be observed in any convenient laboratory time frame. For instance, reaction rate may be expressed in terms of grammoles of aldehyde product produced per liter of catalyst solution per hour of reaction time.

Of course it is to be understood that while the optimization of the subject invention necessary to achieve the best results and efficiency desired are dependent upon one's experience in the utilization of the subject invention, only a certain measure of experimentation should be necessary to ascertain those conditions which are optimum for a given situation and such should be well within the knowledge of one skilled in the art and easily obtainable by following the more preferred aspects of this invention as explained herein. Such optimizations and variations are intended to be within the scope of the claims appended below.

As noted above the hydroformylation reaction conditions that may be employed in the hydroformylation processes encompassed by this invention may include any suitable continuous hydroformylation conditions heretofore disclosed in the above-mentioned patents. For instance, the total gas pressure of hydrogen, carbon monoxide and olefinic unsaturated starting compound of the hydroformylation process may range from about 1 to about 10,000 psia. In general, however, it is preferred that the process be operated at a total gas pressure of hydrogen, carbon monoxide and olefinic unsaturated starting compound of less than about 1500 psia and more preferably less than about 500 psia. The minimum total pressure being limited predominately by the amount of reactants necessary to obtain a desired rate of reaction. More specifically the carbon monoxide partial pressure of the hydroformylation process of this invention is preferable from about 1 to about 120 psia, and more preferably from about 3 to about 90 psia, while the hydrogen partial pressure is preferably about 15 to about 160 psia and more preferably from about 30 to about 100 psia. In general $H_2$:CO molar ratio of gaseous hydrogen to carbon monoxide may range from about 1:10 to 100:1 or higher, the more preferred hydrogen to carbon monoxide molar ratio being from about 1:1 to about 10:1. Further, the hydroformylation process may be conducted at a reaction temperature from about 45° C. to about 150° C. In general hydroformylation reaction temperature of about 50° C. to about 120° are preferred for all types of olefinic starting materials, the more preferred reaction temperatures being from about 50° C. to about 100° C. and most preferably about 95° C.

The olefinic starting material reactants that may be employed in the hydroformylation reactions encompassed by this invention include olefinic compounds containing from 2 to 30 carbon atoms. Such olefinic compounds can be terminally or internally unsaturated and be of straight-chain, branched chain or cyclic structures, as well as be olefin mixtures, such as obtained from the oligomerization of propene, butene, isobutene, etc., (such as so called dimeric, trimeric or tetrameric propylene, and the like, as disclosed, e.g., in U.S. Pat. Nos. 4,518,809 and 4,528,403). Moreover, such olefinic compounds may further contain one or more ethylenic unsaturated groups, and of course, mixtures of two or more different olefinic compounds may be employed as the starting hydroformylation material if desired. Further such olefinic compounds and the corresponding aldehyde products derived therefrom may also contain one or more groups or substituents which do not unduly adversely affect the hydroformylation process or the process of this invention such as described, e.g., in U.S. Pat. Nos. 3,527,809; 4,668,651 and the like.

Illustrative olefinic unsaturated compounds are alpha-olefins, internal olefins, alkyl alkenoates, alkenyl alkanoates, alkenyl alkyl ethers, alkenols, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, 2-ethyl-1-hexene, 2-octene, styrene, 3-phenyl-1-propene, 1,7-octadiene, 3-cyclohexyl-1-butene, hex-1-en-4-ol, oct-1-en-4-ol, vinyl acetate, vinyl propionate, methyl methacrylate, vinyl ethyl ether, vinyl methyl ether, n-propyl-7-octenoate, 3-butenenitrile, 4-pentenenitrile, 3-pentenenitrile, 2-pentenenitrile, 4-pentenoic acid, 3-pentenoic acid, 2-pentenoic acid, methyl-4-pentenoate, methyl-3-pentenoate, methyl-2-pentenoate, ethyl-4-pentenoate, ethyl-3-pentenoate, ethyl-2-pentenoate, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, iso-safrole, anethol, indene, limonene, betapinene, dicyclopentadiene, cyclooctadiene, camphene, linalool, and the like.

Of course, it is understood that mixtures of different olefinic starting materials can be employed, if desired, by the hydroformylation process of the subject invention. More preferably the subject invention is especially useful for the production of aldehydes, by hydroformylating alpha olefins containing from 2 to 20 carbon atoms, including isobutylene, and internal olefins containing from 4 to 20 carbon atoms as well as starting material mixtures of such alpha olefins and internal olefins. Still more preferably the subject invention is especially useful for the production of aldehydes from methyl-pentenoates, in any isomeric form, or mixture thereof. These include methyl-4-pentenonate, trans-methyl-3-pentenonate, cis-methyl-3-pentenonate, trans-methyl-2-pentenonate and cis-methyl-2-pentenonate. It is also to be understood that commercial alpha olefins containing 4 or more carbon atoms may contain minor amounts of corresponding internal olefins and/or their corresponding saturated hydrocarbon and that such commercial olefins need not necessarily be purified from same prior to being hydroformylated.

Illustrative rhodium-bisphosphite complex catalysts employable in such hydroformylation reactions encompassed by this invention may include those disclosed in the above mentioned patents wherein the bisphosphite ligand is a ligand selected from the class consisting of Formulas (I), (II) and (III) above. In general, such catalysts may be preformed, or formed in situ, as described e.g., in said U.S. Pat. Nos. 4,668,651 and 4,769,498, and consist essentially of rhodium in complex combination with the organobisphosphite ligand. It is believed that carbon monoxide is also present and complexed with the rhodium in the active species. The active catalyst species may also contain hydrogen directly bonded to the rhodium.

As noted above illustrative organobisphosphite ligands that may be employed as the bisphosphite ligand complexed to the rhodium catalyst and/or any free bisphosphite ligand (i.e. ligand that is not complexed with the rhodium metal in the active complex catalyst) in such hydroformylation reactions encompassed by this invention include those of Formulas (I), (II), and (III) above.

Illustrative divalent radicals represented by $R^1$ in the above bisphosphite formulas (I), (II) and (III) include substituted and unsubstituted radicals selected from the group consisting of alkylene, alkylene-$(Q)_n$-alkylene, phenylene, naphthylene, phenylene-$(Q)_n$-phenylene and naphthylene-$(Q)_n$-naphthylene radicals, and where Q, and n are the same as defined above. More specific illustrative divalent radicals represented by $R^1$ are shown by the structure of (IV) or (V) wherein $(Q)_n$ is the same as above. These include, 1,1'biphenyl-2,2'-diyl, 3,3'-dialkyl-1,1'-biphenyl-2,2'-diyl, 3,3'-dicarboxy ester-1,1'-biphenyl-2,2'-diyl, 1,1'binaphthyl-2,2'-diyl, 3,3'-dicarboxy ester-1,1'-binaphthyl-2,2-diyl, 3,3'-dialkyl-1,1'-binaphthyl-2,2-diyl, 2,2'-binaphthyl-1,1'-diyl, phenylene-$CH_2$-phenylene, phenylene-O-phenylene, phenylene-$CH(CH_3)$-phenylene radicals, and the like.

Illustrative radicals represented by $Z^1$, $Z^2$, $Z^3$, $Z^4$, $Z^5$, $Z^6$, $Z^7$, $Z^8$, $Z^9$, $Z^{10}$, and $Z^{11}$ in above Formulas (IV) to (IX), in addition to hydrogen, include any of those organic substituents containing from 1 to 18 carbon atoms, disclosed in U.S. Pat. No. 4,668,651, or any other radical that does not unduly adversely effect the process of this invention. Illustrative radicals and substituents encompass alkyl radicals, including primary, secondary and tertiary alkyl radicals such as methyl, ethyl n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; condensated aryl radicals such as phenylene, naphthylene, and the like, alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy —$OCH_2CH_2OCH_3$, —$(CH_2CH_2)_2OCH_3$, —$O(CH_2CH_2)_3OCH_3$, and the like; aryloxy radicals such as phenoxy and the like; as well as silyl radicals such as —$Si(CH_3)_3$, —$Si(OCH_3)_3$, —$Si(C_3H_7)_3$, and the like; amino radicals such as —$NH_2$, —$N(CH_3)_2$, —$NHCH_3$, —$NH(C_2H_5)$, and the like; acyl radicals such as —$C(O)CH_3$, —$C(O)C_2H_5$, —$C(O)C_6H_5$, and the like; carbonyloxy radicals such as —$C(O)OCH_3$, —$C(O)OCH(CH_3)_2$—$(C(O)CH(CH_3)C_8H_{17}$, and the like; oxycarbonyl radicals such as —$(CO)C_6H_5$, and the like; amido radicals such as —$CONH_2$, —$CON(CH_3)_2$, —$NHC(O)CH_3$, and the like; sulfonyl radicals such as —$S(O)_2C_2H_5$ and the like; sulfinyl radicals such as —$S(O)CH_3$ and the like; thionyl radicals such as —$SCH_3$, —$SC_2H_5$, —$C_6H_5$, and the like; phosphonyl radicals such as —$P(O)(C_6H_5)_2$, —$P(O)(CH_3)_2$, —$P(O)(C_2H_5)_2$, —$P(O)(C_3H_7)_2$, —$P(O)CH_3(C_6H_5)$, —$P(O)(H)(C_6H_5)$, and the like.

Illustrative radicals represented by $X^1$, $X^2$, $X^3$, $X^4$, $X^5$ and $X^6$ in above Formulas (IV) to (IX) include those illustrated and discussed above as representing $Z^1$ to $Z^{11}$, and condensated aryl radicals.

Illustrative radicals represented by $Y^1$, $Y^2$, $Y^3$, $Y^4$ and $Y^5$ in above Formulas (IV) to (IX) include those illustrated and discussed above as representing $Z^1$ to $Z^{11}$, except condensated aryl radicals.

More preferably, $X^1$ is the same as $X^2$ and $Z^1$ is the same as $Z^2$ in Formula (IV), $X^3$ is the same as $X^4$, $Z^3$ is the same as $Z^4$, and $Y^1$, $Y^2$ are hydrogen radicals in Formula (V), $Z^6$ is a hydrogen radical in Formula (VII), $Z^8$ is the same as $Z^9$ in Formula (VIII), $Z^{10}$ is the same as $Z^{11}$ and $Y^4$ and $Y^5$ are hydrogen radicals in Formula (IX).

Specific illustrative examples of the bisphosphite ligands employable in this invention include such preferred ligands as:

3,3'-bis(carboxyisopropyl)-1,1'-binaphthyl-2,2-diyl-bis[bis(1-naphthyl)]phosphite having the formula:

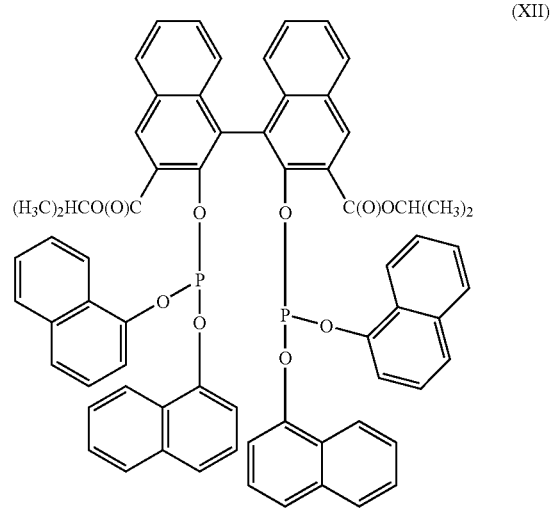

(XII)

[3,3'-bis(t-butyl)-5,5'-dimethoxy-1,1'-biphenyl-2,2'-diyl]-bis(oxy)]-bis(dibenzo[d,f][1,3,2]dioxaphosphepin having the formula:

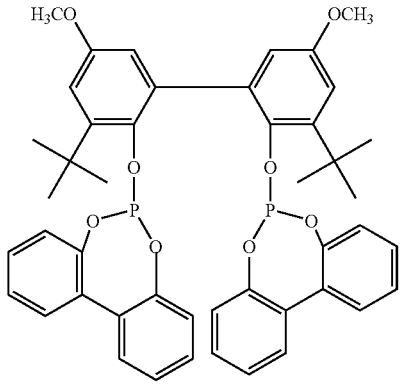

3,3'-bis(carboxyisopropyl)-1,1'-binaphthyl-2-yl-bis[(1-naphthyl)]phosphite-2'-yl-oxy-dibenzo[d,f][1,3,2]dioxaphosphepin having the formula:

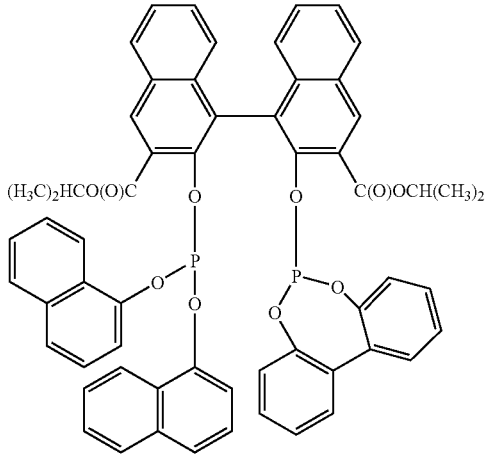

5,5'-bis(t-butyl)-3,3'-dimethoxy-1,1'-biphenyl-2,2'-diyl-bis[bis(1-naphthyl)]phosphite having the formula:

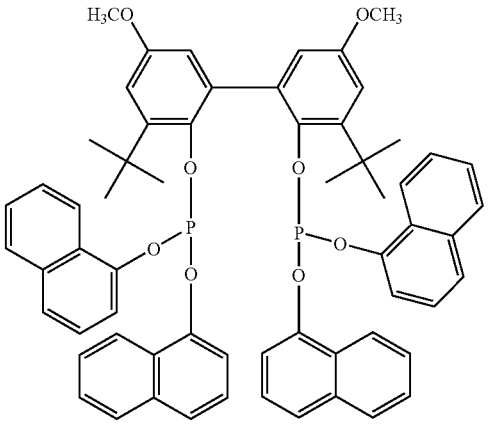

3,3'-bis(carboxymethyl)-1,1'-binaphthyl-2,2'-diyl-bis[bis(2,5-di-t-butyl)]phosphite having the formula:

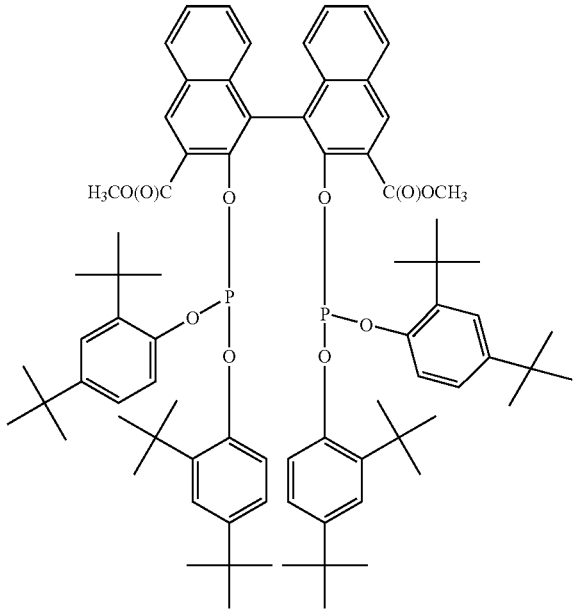

[3,3'-bis(t-butyl)-5,5'-dimethoxy-1,1'-biphenyl-2,2'-diyl]-bis(oxy)]-bis([1,1'-dinaphto[d,f][1,3,2])dioxaphosphepin having the formula:

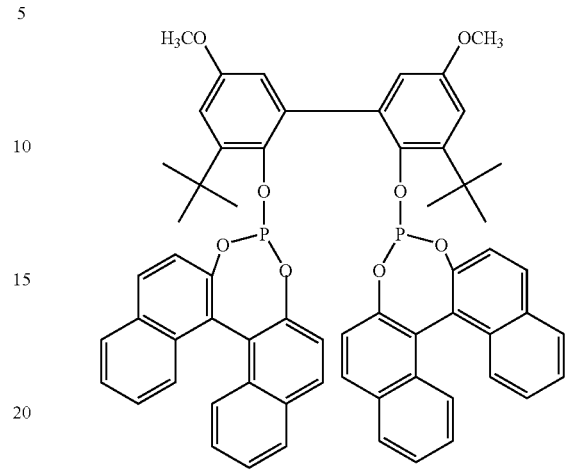

and the like.

Such types of bisphosphite ligands employable in this invention and/or methods for their preparation are well known as seen disclosed for example in U.S. Pat. Nos. 4,668,651; 5,288,918; 5,710,306, the entire disclosure of which is incorporated herein by reference thereto.

Finally, the aldehyde products of the hydroformylation process of this invention have a wide range of utility that is well known and documented in the prior art e.g. they are especially useful as starting materials for the production of alcohols and acids, as well as for the production of polymeric compounds such as plastics.

The following examples are illustrative of the present invention and are not to be regarded as limitative. It is to be understood that all of the parts, percentages and proportions referred to herein and in the appended claims are by weight unless otherwise indicated.

EXAMPLE 1

A 2 g (1.835 mmol) quantity of naphthol-3 ligand (see structure XII above) was added to a slurry of an equivalent amount of (0.473 g, 1.835 mmol) green crystalline $Rh(CO)_2AcAc$ (AcAc=acetylacetonate) in 35 mL dry, degassed toluene under an atmosphere of $N_2$ at room temperature. Upon the addition intensive CO gas development took place and a clear yellow solution was formed. $^{31}P$ NMR spectrum taken from the obtained yellow solution showed only one doublet peak, which appeared at 131.3 ppm with a $J_{Rh-P}$ coupling of 301 Hz. The relatively large Rh-P coupling indicates the presence of a four-coordinate Rh-complex. $^{13}C$ NMR spectrum from the solution showed the presence of a coordinated $AcAc^-$ group as well as of the liberated (and dissolved) CO. Accordingly, the species can be assigned to Rh(naphthol-3)(Acac) complex. When the yellow solution of the latter complex was pressurized to 150 psia with a 1/1 mixture of $CO/H_2$ and heated to 100° C. a nearly colorless solution formed instantaneously. The reaction can be monitored by using a small portion (~2 mL) of the Rh(naphthol-3)(Acac) solution under identical conditions in a sapphire high-pressure (HP) NMR tube. The reaction of Rh(naphthol-3)(Acac) with $CO/H_2$ is so fast that by the time 100° C. is reached inside the HP NMR tube (about 5 min. is required), the $^{31}$P NMR shows the complete transformation of Rh(naphthol-3)(Acac) to one new species, which exhibited one doublet peak in the $^{31}$P NMR spectrum appearing at 151.9 ppm with a $J_{Rh-P}$ coupling of 239.4 Hz at 100° C. (δ 152.3 ppm, $J_{Rh-P}$=239.9 Hz at room temperature). Similarly, when a small aliquot of the Rh(naphthol-3)(Acac) solution was heated to 100° C. under a 150 psia atmosphere of a 1/1 mixture of $^{13}$CO/H$_2$, the same single doublet peak was observed on the $^{31}$P NMR spectrum. However, cooling solution to room temperature resulted in a colorless solution, which showed splitting of the doublet pattern into a doublet of triplets by two additional small, 15.8 Hz couplings in the $^{31}$P NMR. These couplings can be assigned to the coupling between two coordinated $^{13}$Co molecules with the coordinated P-atoms of the ligand. The room temperature $^{13}$C NMR spectrum of the complex showed two different sets of multiplets for the coordinated carbonyl groups at 194.4 ppm and 193.3 ppm. In accordance with the $^{31}$P NMR spectrum, the $J_{P-C}$ couplings were no longer detectable in the $^{13}$C NMR spectrum at 100° C. due to fast exchange between the coordinated carbonyl groups and free $^{13}$Co. The $^{13}$C NMR spectrum also showed the presence of liberated acetylacetone. The $^1$H NMR spectra from the solution at room temperature or lower showed a characteristic hydride resonance at −10.4 ppm (multiplet, $J_{P-H}$=4.2 Hz, $J_{Rh-H}$=9.0 Hz). These NMR data and and other analytical methods such as IR confirm the exclusive presence of HRh(CO)$_2$(naphthol-3) complex (X) in the solutions above. HRh(CO)$_2$(naphthol-3) forms similarly fast by using other precursors such as [Rh(CO)$_2$Cl]$_2$ or [RhCl(COD)]$_2$ (COD=cyclooctadiene) under hydroformylation process conditions and in solvents other than toluene. For example, the hydride complex can also be exclusively obtained under similar conditions (100° C., 150 psia of CO/H$_2$=1/1) in methyl-5-formylvalerate containing 0–80% of methyl-3-pentenoate and its isomers and 0–10% of monomethyladipate. Naturally, when an olefinic substrate such as methyl-3-pentenoate is present in the catalyst solution, heating to 100° C. under syn-gas pressure initiates the hydroformation reaction. This way an operating hydroformylation system can be made in a HP NMR tube, which can be conveniently monitored by NMR spectroscopy. Monitoring such systems it was shown that HRh(CO)$_2$(naphthol-3) remains the exclusive Rh-component until both methyl-3-pentenoate and syn-gas are readily available (present in an excess amount compared to Rh). The above described hydrido complex was found also the dominating species by taking off-line $^{31}$P NMR samples from a continuously operated reactor, in which hydroformylation of methyl-3-pentenoate was carried out by using naphtol-3 as a ligand under various reaction conditions (i.e. at different temperatures, pressures, CO/H$_2$ ratios, substrate/Rh ratios, Rh-concentrations etc.).

EXAMPLE 2

The solution of 1.835 mmol of HRh(CO)$_2$(naphthol-3) in 35 mL toluene obtained in Example 1 was cooled to room temperature and the CO/H$_2$ pressure was released.

An amount of 5 mL (~40 mmol) of freshly distilled methyl-3-pentenoate was added to the solution under N$_2$. The solution was pressurized then to 150 psia with CO alone and heated at 140° C. for 2 hours. After cooling back the solution the CO-pressure was released and the formed yellow solution was transferred into a Schlenk-tube under an atmosphere of N$_2$. $^{31}$P NMR taken from the solution showed a complete conversion of the hydride complex described in Example 1 to a new species, exhibiting doublet of doublets at 179.5 ppm ($J_{Rh-p}$=233.8 Hz, $J_{P-P}$=267.5 Hz) and at 138.5 ppm ($J_{Rh-P}$=225.6 Hz, $J_{P-P}$=267.5 Hz). The obtained yellow solution was then concentrated in vacuum. The obtained yellow residue was recrystallized from a mixture of CO-saturated butylacetate and hexane with 70% (1.6 g) yield to a pure beige crystalline solid, which was suitable for x-ray crystallographic analysis. A drawing of the found absolute structure is shown in FIG. 1.

This exhibits a trigonal bypiramidal structure and orthometallation of one of the naphthyl groups. The P-atoms of the complex are situated in equatorial position (planar position) with one CO being equatorial and the other apical bound to Rh. The 2-naphthyl carbon of one of the naphtoxy groups is bound to Rh in the other remaining apical position. The crystal unit contains one butyl, acetate molecule which crystallizes with the complex. Spectroscopical methods, such as $^{31}$P NMR (above),$^{13}$C NMR and IR were in agreement with this structure in solution after redissolving the obtained crystalline material in various solvents. Thus, for example when the isolated orthometallated complex (XI) was dissolved in toluene and heated under 150 psia of $^{13}$CO to 100° C., $^{31}$P NMR showed the same spectrum as above. $J_{P-C}$ couplings were not observed due to the fast exchange between coordinated carbonyl groups and free $^{13}$Co. However, a subsequent cooling to room temperature resulted in a splitting of both $^{31}$P signals by two additional $J_{P-C}$ couplings analogous to what observed above with the hydride. Thus, the pattern at 179.5 ppm (P, which is bound to methallated naphthyl group) and 138.5 ppm was supplemented with $J_{P1-C1}$=59.5 Hz, $J_{P1-C2}$=16.2 Hz and $J_{P2-C1}$=46.7 Hz, $J_{P2-C2}$=17.5 Hz couplings, respectively. These $J_{P-C}$ couplings were also observed on the $^{13}$C NMR spectrum, which exhibited two different multiplet signals at 194.0 and 190.9 ppm at room temperature. From the two sets of carbonyl signals the one at 194.0 ppm can be assigned to the apical carbonyl groups based on the size of observed $J_{P-C}$ coupling. The large difference in the $J_{P-C}$ couplings of the apical and planar CO groups in the orthometallated complex indicates a much higher conformational stability as compared to the hydride complex in Example 1, which showed equal values $J_{P-C}$ and other signs of conformational lability.

EXAMPLE 3

A 30 mg sample of complex (XI), obtained from example 2 was dissolved in 1.6 mL dry, degassed toluene in a HP NMR tube under an atmosphere of N$_2$. The tube was then pressurized to 700 psia with syn-gas (CO/H$_2$=1/1) and heated to 100° C. After 5 minutes at 100° C., $^{31}$P NMR showed a complete conversion of the orthomethallated complex (XI) to the hydride complex (X), which is described above in Example 1. As shown in Examples 7 and 8, the formation of the hydride complex is similarly fast and quantitative in solvents other than toluene such as in methyl-3-pentenoate or in methyl-5-formylvalerate at 100° C. under similar pressure. This example demonstrates that the orthometallated complex (XI) can be readily converted to the catalytically active hydride complex in the presence of low pressure syn-gas.

EXAMPLE 4

A 40 mg sample complex (XI), obtained from example 2 was dissolved in 1.6 mL dry, degassed toluene in a HP NMR tube under an atmosphere of $N_2$. The tube was pressurized then to 700 psia with CO containing 0.3 v % $H_2$ and heated to 100° C. After 5 minutes at 100° C., 31 P NMR showed the formation of the hydride complex (X) and the expense of orthometallated complex (XI). The formation of the hydride complex continued until about 1 hour at 100° C., when 50% conversion was reached from the orthometallated (XI) to the hydride complex (X). Calculating the amount of added $H_2$ (0.36 n mL, 0.016 mmol) in with the gas mixture showed that practically all the available hydrogen was consumed in this reaction. As a fact, the orthometallated complex (XI) is so sensitive for reaction with residual hydrogen that it can be used to trace several ppm residual hydrogen content as contaminant in CO gas. This example demonstrates that residual hydrogen prefers to be present as coordinated instead of dissolved molecular hydrogen.

EXAMPLE 5

A 21.8 mg (0.02 mmol) sample of naphthol-3 and 5.1 mg (0.02 mmol) $Rh(CO)_2(AcAc)$ were added to 2.0 mL dry, degassed toluene in a HP NMR tube at room temperature under an atmosphere of $N_2$. The tube was pressurized to 150 psia with syn-gas ($CO/H_2$) and heated to 100° C. After 5 min heating at 100° C., the complete formation of the hydrido complex (X) was observed by $^{31}P$ NMR, which is described in example 1. The tube was then cooled to room temperature and the syn-gas pressure was released under an atmosphere of $N_2$. An amount of 25 µL (0.2 mmol) t-2 hexene was added and the tube was pressurized to 150 psia with CO. The tube was heated to 100° C. and the reaction was followed by NMR spectroscopy. $^{31}P$ NMR showed a complete conversion of the hydrido complex (X) to the orthometallated complex (XI), which is described in example 2, after 2 hours heating at 100° C. This example demonstrates that olefins other than methyl-3 pentenoate can also be used for removing coordinated and free hydrogen content from a hydroformylation reaction mixture.

EXAMPLE 6

The experiment in example 5 was repeated, except that 23 µL (0.2 mmol) methyl-3-pentenoate was added instead of t-2-hexene. $^{31}P$ NMR showed a complete conversion of the hydrido complex (X) to the orthometallated complex (XI), which is described in example 2, after 1 hour heating at 100° C. This example demonstrates that methyl-3 pentenoate is more effective for removing coordinated and free hydrogen content from a hydroformylation reaction mixture than t-2-hexene.

EXAMPLE 7

A 21.8 mg (0.02 mmol) sample of naphthol-3 and amount of 5.1 mg (0.02 mmol) $Rh(CO)_2(AcAc)$ was added to 2.5 mL (20 mmol) of dry, degassed methyl-3-pentenoate in a HP NMR tube at room temperature under an atmosphere of $N_2$. The tube was pressurized to 150 psia with syn-gas ($CO/H_2$) and heated to 100° C. After 5 min heating at 100° C., the complete formation of the hydrido complex (X) was observed by $^{31}P$ NMR, which is described in example 1. The tube was then cooled to room temperature and the syn-gas pressure was released under an atmosphere of $N_2$. The tube was pressurized again to 150 psia with CO. The tube was heated to 100° C. and the reaction was followed by NMR spectroscopy. $^{31}P$ NMR showed a complete conversion of the hydrido complex (X) to the orthometallated complex (XI), which is described in example 2, after 5–6 minutes heating at 100° C. This example demonstrates that an increase in the olefin concentration accelerates the removal of coordinated and free molecular hydrogen content from a hydroformylation reaction mixture.

EXAMPLE 8

A 300 mg sample of complex (XI), obtained from Example 2 was dissolved in 30 mL methyl-5-formylvalerate containing about 40% methyl-3-pentenoates in an autoclave under an atmosphere of $N_2$. The autoclave was pressurized then to 150 psia with syn-gas ($CO/H_2=1/1$) and heated at 100° C. for 10 minutes. After cooling and venting, the colorless solution was transferred from the autoclave to a Schlenk tube under an atmosphere of $N_2$. A $^{31}P$ NMR sample taken from the solution showed the exclusive presence of the hydride complex (X). A distillation head was fitted to the Schlenk-tube and the solution was heated to 100° C. under 0.03 psia vacuum. The solution was than further heated under continuous slow distillation and reflux in high vacuum. After 85 minutes, a $^{31}P$ NMR sample was taken from the solution, which showed less than 30% conversion of the hydride complex (X) to the orthometalled complex (XI). The solution was heated then for an additional 4.5 hours at 100° C. under the same conditions in high vacuum at 100° C., which resulted in 90% conversion of the hydride compound to the orthomethallated complex. This example demonstrates the vacuum distillation is not as effective method for removing coordinated and free hydrogen content from a hydroformylation reaction mixture as the ones, which are described in examples 5–7.

EXAMPLE 9

A 45 mg sample of complex (XI), obtained from example 2, and 27 mg of tris(orthotolyl)phosphine (used as internal standard for the $^{31}P$ NMR measurements below) were dissolved in 1.8 mL of dry, degassed toluene containing less than 50 ppm water in a HP NMR tube under an atmosphere of $N_2$. The tube was pressurized then to 120 psia with CO and heated at 100° C. for 5 days. After 5 days the heating the clear yellow solution was then cooled to room temperature and a $^{31}P$ NMR specrtrum was recorded. This showed only a marginal, ~3% degradation of the orthometallated complex to ligand-oxides, which appeared at −17.8 and −18.8 ppm. No hydrolysis or other ligand degradation process was observed. The pressure was then released from the HP NMR tube under an atmosphere of $N_2$ and the tube was pressurized again to 150 psia with syn-gas ($CO/H_2=1/1$). The tube was heated again to 100° C. After 5 minutes at 100° C., a $^{31}P$ NMR spectrum was taken, which indicated a complete conversion of the orthometallated complex (XI) to the hydride (X) with the residual 3% ligand-oxide content. The solution was then heated at 100° C. for 3 days upon which a significant amount of Rh-black separated. After cooling back to room temperature, a $^{31}P$ NMR was taken. This showed about 25% degradation of the hydride complex (X) to three singlet peaks appearing between 8.5 and 10 ppm and an unchanged 3% oxide content. The peaks between 8–10 ppm are assigned to acidic hydrolysis degradation products of the ligand. This experiment demonstrates that the orthomethallated complex (XI) is more stable to hydrolysis than the hydride complex (X).

EXAMPLE 10

A 34 mg sample of complex (XI), obtained from example 2, and 21 mg of tris(orthotolyl)phosphine (used as internal standard for the $^{31}$P NMR measurements below) was dissolved in 1.8 mL of dry, degassed toluene containing less than 50 ppm water in a HP NMR tube under an atmosphere of $N_2$. The tube was pressurized then to 700 psia with CO and heated at 100° C. for 5 hrs. $^{31}$P NMR showed no degradation of the orthometallated complex in the clear yellow solution. The pressure was then released from the HP NMR tube under an atmosphere of $N_2$ and the solution was degassed from CO by bubbling $N_2$ into the solution. An amount of 100 μL of dry, distilled methyl-3-pentenoate was added and the tube was closed under an atmosphere of $N_2$. The tube was heated at 100° C. for 1 day. $^{31}$P NMR recorded after the heating showed less than 2% degradation of the orthometallated complex to ligand-oxides. No sign of ligand hydrolysis was detected. The experiment demonstrates that the orthometallated complex (XI) is stable against hydrolysis in the absence of CO.

While the invention has been described in terms of preferred embodiments the skilled artisan will appreciate that various modifications, substitutions, omissions and changes may be made without departing from the scope thereof. Accordingly, it is intended that the scope of the present invention be limited solely by the scope of the claims provided below, included equivalents thereof.

The invention claimed is:

1. A hydroformylation process comprising:
   A) reacting an olefinically unsaturated compound comprising from 2 to 30 carbon atoms with carbon monoxide and hydrogen in the presence of a rhodium-bisphosphite complex catalyst to produce a mixture to be distilled comprising an aldehyde reaction product or products and a catalyst;
   B) reducing or eliminating the amount of dissolved and chemically bound molecular hydrogen in the mixture to be distilled; and
   C) separating the aldehyde product from the catalyst from the mixture to be distilled by means of distillation; wherein:
   D) said catalyst complex has at least a first and second state;
   E) said second state is more thermally stable and/or more stable against hydrolysis than the first state;
   F) reducing or eliminating the amount of hydrogen in the mixture to be distilled allows for most or all of the catalyst in the mixture to be in the more thermally and/or hydrolytic stable state, wherein reducing or eliminating the amount of hydrogen in the mixture to be distilled comprises adding an olefin to the mixture to be distilled.

2. The process of claim 1 wherein reducing or eliminating the amount of hydrogen in the mixture to be distilled comprises stripping the mixture with a gas.

3. The process of claim 2 wherein said gas is an inert gas.

4. The process of claim 2 wherein said gas is carbon monoxide.

5. The process according to claim 1 wherein reducing or eliminating the amount of hydrogen in the mixture to be distilled comprises adding an olefin and carbon monoxide to the mixture to be distilled.

6. The process according to claim 1, wherein the bisphosphite ligand of said complex catalyst is a ligand of a formula selected from the group consisting of:

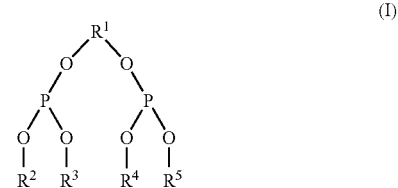

(I)

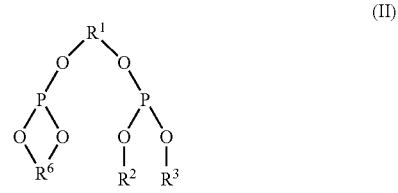

(II)

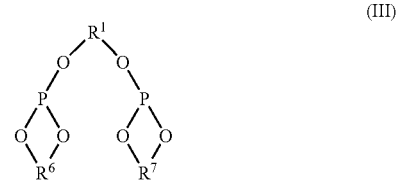

(III)

wherein each $R^1$ represents a divalent radical selected from a group consisting of alkylene, alkylene-$(Q)_n$-alkylene, arylene and arylene-$(Q)_n$-arylene, and wherein each alkylene radical individually contains from 2 to 18 carbon atoms and is the same or different, and wherein each arylene radical individually contains from 6 to 18 carbon atoms and is the same or different; wherein each Q individually represents a divalent bridging group of —O— or —CR'R'' wherein each R' and R'' radical individually represents hydrogen or a methyl radical; and wherein each n individually has a value of 0 or 1, wherein $R^2$, $R^3$, $R^4$, and $R^5$ may be the same or different and each is individually represented by the structure of (VI) or (VII),

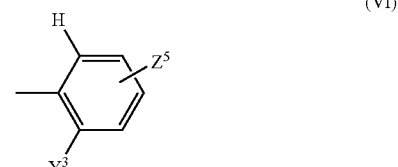

(VI)

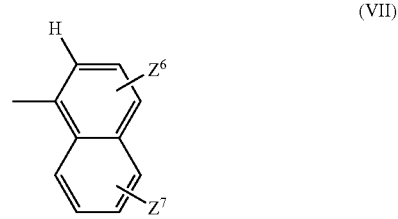

(VII)

wherein $R^6$ and $R^7$ may be the same or different and each is individually represented by the structure of (VIII) or (IX),

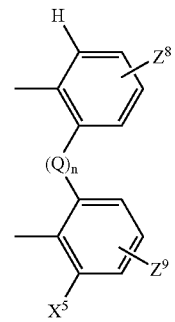
(VIII)

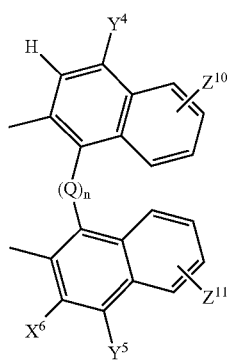
(IX)

wherein $X^5$ and $X^6$ may be the same or different and each individually represents an organic radical, wherein $Y^1$, $Y^2$, $Y^3$, $Y^4$ and $Y^5$ are the same or different and each represents a hydrogen or alkyl radical, wherein $Z^5$, $Z^6$, $Z^7$, $Z^8$, $Z^9$, $Z^{10}$ and $Z^{11}$ may be the same or different and each represent a hydrogen or an organic radical placed at any remaining position of the aryl rings.

7. The process according to claim 6, wherein $R^1$ is represented by the structure of (IV), (V),

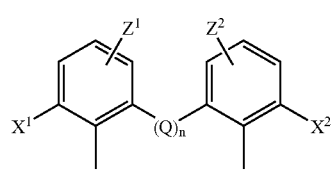
(IV)

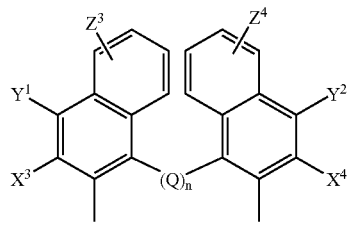
(V)

(VIII) or (IX), wherein $X^1$, $X^2$, $X^3$, and $X^4$ may be the same or different and each individually represents an organic radical, wherein $Y^1$ and $Y^2$ are the same or different and each represents a hydrogen or alkyl radical, wherein $Z^1$, $Z^2$, $Z^3$, and $Z^4$ may be the same or different and each represent a hydrogen or an organic radical placed at any remaining position of the aryl rings, wherein $X^1$ is the same as $X^2$ and $Z^1$ is the same as $Z^2$ in Formula (IV), $X^3$ is the same as $X^4$, $Z^3$ is the same as $Z^4$, and $Y^1$ and $Y^2$ are hydrogen radicals in Formula (V), $Z^8$ is the same as $Z^9$ in Formula (VIII), $Z^{10}$ is the same as $Z^{11}$ and $Y^4$ and $Y^5$ are hydrogen radicals in Formula (IX).

8. The process according to claim 6, wherein the ligand used is selected from the group consisting of [3,3'-bis(t-butyl)-5,5'-dimethoxy-1,1'-biphenyl-2,2'-diyl]-bis(oxy)]-bis(dibenzo[d,f][1,3,2])dioxaphosphepin, 3,3'-bis(carboxyisopropyl)-1,1'-binaphthyl-2,2-diyl-bis[bis(1-naphthyl)] phosphite and 3,3'-bis(carboxymethyl)-1,1'-binaphthyl -2,2'-diyl-bis[bis(2,5-di-t-butyl)]phosphite.

9. The process according to claim 1, wherein the total amount of molecular hydrogen present in the distillation mixture is no more than 2 ppm, relative to the total weight of the distillation mixture.

10. The process according to claim 1 wherein the total amount of molecular hydrogen present in the distillation mixture is no more than 0.1 ppm, relative to the total weight of the distillation mixture.

11. The process according to claim 2, wherein the stripping is carried out between 0.1 and 1000 psia pressure and a temperature between 40° C. and 150° C.

12. The process according to claim 2, wherein the stripping is carried out between 1 and 100 psia pressure and a temperature between 80° C. and 120° C.

13. The process according to claim 5, wherein the mixture after an olefin and CO is added is pressurized by using a CO pressure between 10 and 1000 psia and a temperature between 40° C. and 150° C.

14. The process according to claim 5, wherein the mixture after an olefin and CO is added is pressurized by using a CO pressure between 20 and 300 psia and a temperature between 80° and 120° C.

* * * * *